(12) United States Patent
Halevi

(10) Patent No.: US 7,309,158 B2
(45) Date of Patent: Dec. 18, 2007

(54) DIGITAL DENTAL X-RAY SENSOR PROTECTOR

(75) Inventor: Tzipora Halevi, Elmsford, NY (US)

(73) Assignee: AFP Imaging Corporation, Elmsford, NY (US)

( * ) Notice: Subject to any disclaimer, the term of this patent is extended or adjusted under 35 U.S.C. 154(b) by 0 days.

(21) Appl. No.: 11/191,719

(22) Filed: Jul. 28, 2005

(65) Prior Publication Data

US 2007/0025523 A1  Feb. 1, 2007

(51) Int. Cl.
*A61B 6/14* (2006.01)
(52) U.S. Cl. .................................................. 378/191
(58) Field of Classification Search ............... 378/191, 378/190, 189, 188, 168, 210, 184; 433/25, 433/27, 29
See application file for complete search history.

(56) References Cited

U.S. PATENT DOCUMENTS

| | | | | |
|---|---|---|---|---|
| 5,434,418 A | * | 7/1995 | Schick | 250/370.11 |
| 5,677,537 A | * | 10/1997 | Pfeiffer | 250/370.09 |
| 6,527,442 B2 | * | 3/2003 | Carroll | 378/189 |
| 7,004,627 B2 | * | 2/2006 | Strong | 378/168 |
| 2005/0013412 A1 | * | 1/2005 | Calderwood et al. | 378/170 |
| 2005/0228307 A1 | * | 10/2005 | Gibree | 600/549 |
| 2005/0265522 A1 | * | 12/2005 | Manley | 378/169 |
| 2006/0115053 A1 | * | 6/2006 | Nanni et al. | 378/170 |

* cited by examiner

*Primary Examiner*—Edward J. Glick
*Assistant Examiner*—Anastasia S. Midkiff
(74) *Attorney, Agent, or Firm*—Cooper & Dunham LLP

(57) ABSTRACT

A protector for a digital dental x-ray sensor reduces damage to the sensor and pain to a patient associated with the placement of the sensor into a patient's oral cavity. The protector has two flexible, substantially rectangular wall members secured to one another by a perimeter wall member and having a perimeter slot adapted to receive the sensor and to contain the sensor entirely within the wall members.

7 Claims, 2 Drawing Sheets

DIGITAL DENTAL X-RAY SENSOR PROTECTOR

TECHNICAL FIELD

This application relates to dental radiography, and more specifically to protective coverings for digital dental x-ray sensors.

BACKGROUND

Radiography has long been considered an essential procedure in the fields of medicine, dentistry, and veterinary medicine. Today, there is a wide application of radiography for diagnosis and treatment.

Methods and devices using film cartridges are known in the art. Traditional methods and devices utilize periapical and bite-wing film packets. Periapical film packets provide a complete x-ray of a tooth from the crown to the root. Bite-wing film packets, on the other hand, are commonly used to detect interproximal cavities and do not require exposure of the root tips.

Filmless radiography methods and devices are also known in the art. Digitized dental radiography is a procedure for examining a patient's teeth using significantly less radiation than traditional film dental x-rays. The procedure uses a sensor that is placed in the patient's mouth, and a source of gamma radiation is directed toward the sensor. The sensor relates to pixels in an array which are influenced by the gamma radiation passing through the patient's teeth, and the pixels form an image which can be transmitted to a monitor for real-time viewing. One benefit of the procedure is that the amount of radiation needed to activate the sensor is far less than the amount of radiation that the patient is exposed to during the traditional film x-ray procedure. Another benefit is that real-time evaluation of images allows for repositioning of the sensor or acquisition of more images if needed without the delay associated with developing traditional film x-ray images. The images may have a higher resolution than traditional film x-rays and can be manipulated using software to zoom and contrast, making diagnostics more precise.

FIG. 1 shows a digital sensor that is used in dental radiography. A digital sensor also is disclosed in U.S. Pat. No. 6,527,442 to Carroll. The sensors come in various sizes to accommodate different patients, and the sensor is connected to a cable that includes at one end a connection used to connect to a computer. When the sensor is exposed to gamma radiation, the sensing elements generate signals that are transferred to the computer to form an image. Suitable software converts the signal to this image, which may be processed and displayed on a monitor for viewing.

One disadvantage associated with the sensor is the possible damage that the sensor may incur upon insertion into the oral cavity of a patient. Moisture, biting, and other potentially damaging factors may damage or destroy the sensor when used intra-orally.

Another disadvantage associated with the sensor is the pain and discomfort that the patient may be incur when the sensor is used intra-orally. The edges and corners of the sensor may abrade the gums and soft tissues of the mouth, causing significant discomfort or even pain. Gauze and other sterile coverings wrapped around the sensor add bulk and may become loose from the sensor, causing the patient to choke.

Yet another disadvantage associated with the sensor is the need to sterilize the sensor unit after use. Sterilization with autoclaving or radiation processes may damage or destroy the sensor.

Accordingly, there is a need for a protective device for a dental x-ray sensor which is not only simple to use, inexpensive and effective, but, further, which can be readily applied and removed from the dental x-ray sensor and re-used when desired.

SUMMARY OF THE INVENTION

It is therefore a primary object of the present invention to provide a device which serves to protect a digital dental x-ray sensor from moisture, biting and other potentially damaging factors when used intra-orally.

It is another object of the present invention to provide a device which serves to reduce or avoid the pain and discomfort associated caused by the sharp edges and corners of digital dental x-ray sensors when used intra-orally.

It is another object of the present invention to provide a device which serves to minimize bulk and eliminate the need to use adhesive materials when using digital dental x-ray sensors.

It is still a further object of the present invention to provide a protector for a digital dental x-ray sensor which is simple to construct and easy for a dentist or dental technician or veterinarian to use.

Accordingly, the present invention is directed to a device for use in combination with a digital dental x-ray sensor for reducing damage to such a sensor and pain to a patient associated with the placement of such a sensor into the oral cavity of the patient. The device, formed in a single molding operation, comprises two flexible, substantially rectangular wall members secured to one another by a perimeter wall member and having a perimeter slot adapted to receive the digital dental x-ray sensor and to contain the sensor entirely within the wall members.

The present invention is further directed to a method of reducing damage to a digital dental x-ray sensor and pain to a patient associated with the placement of such a sensor into the oral cavity of the patient wherein the method includes the steps of:

(a) providing a protector comprised of two flexible, substantially rectangular wall members, the wall members secured to one another by a perimeter wall member, and having a perimeter slot, the perimeter slot adapted to receive a dental x-ray sensor;

(b) inserting a dental x-ray sensor through the perimeter slot of the dental x-ray sensor protector, such that the sensor is contained entirely within the wall members;

(c) placing the dental x-ray sensor protector and associated dental x-ray sensor into the oral cavity of a patient;

(d) imaging the patient's tooth;

(e) removing the dental x-ray sensor protector and associated dental x-ray sensor from the oral cavity of the patient; and (f) removing the dental x-ray sensor from the dental x-ray sensor protector for further processing.

BRIEF DESCRIPTION OF DRAWINGS

The features of the present application can be more readily understood from the detailed description below with reference to the accompanying drawings herein.

DETAILED DESCRIPTION

Figure 1:
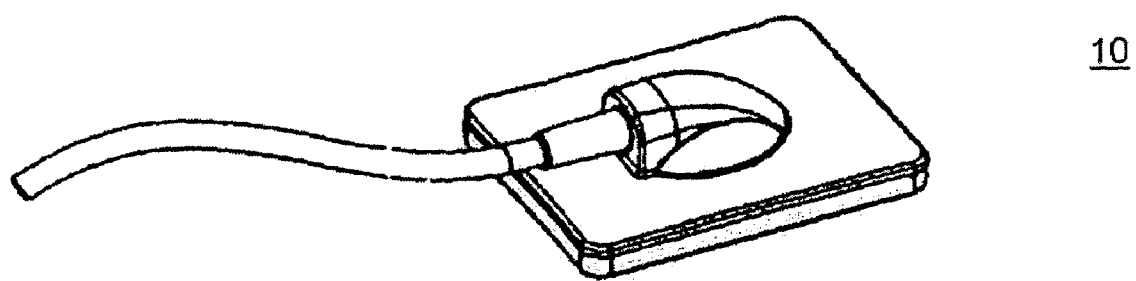
FIG. 1 is a perspective of a digital dental x-ray sensor used in radiography procedures.
Figure 2:
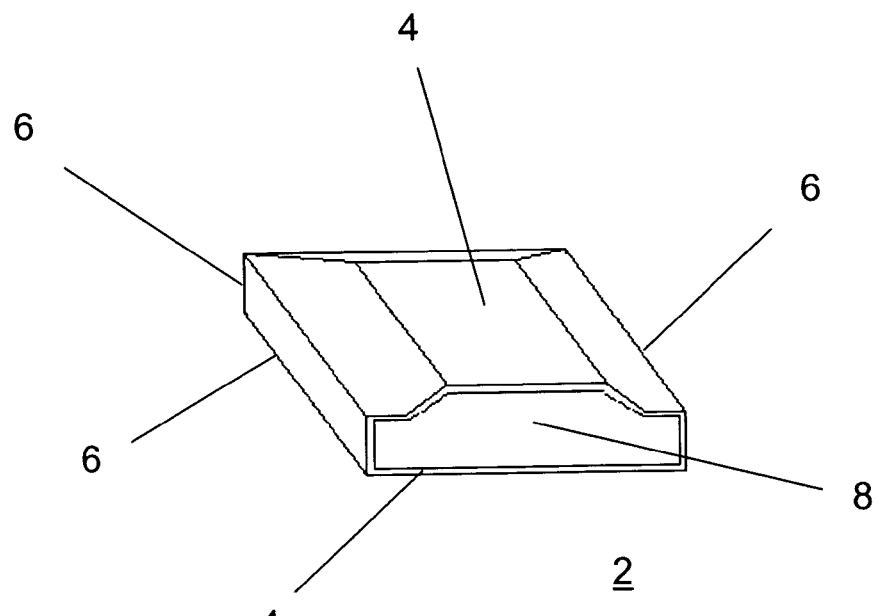
FIG. 2 is a perspective view of the digital dental x-ray sensor protector in accordance with an embodiment of the present invention.
Figure 3:
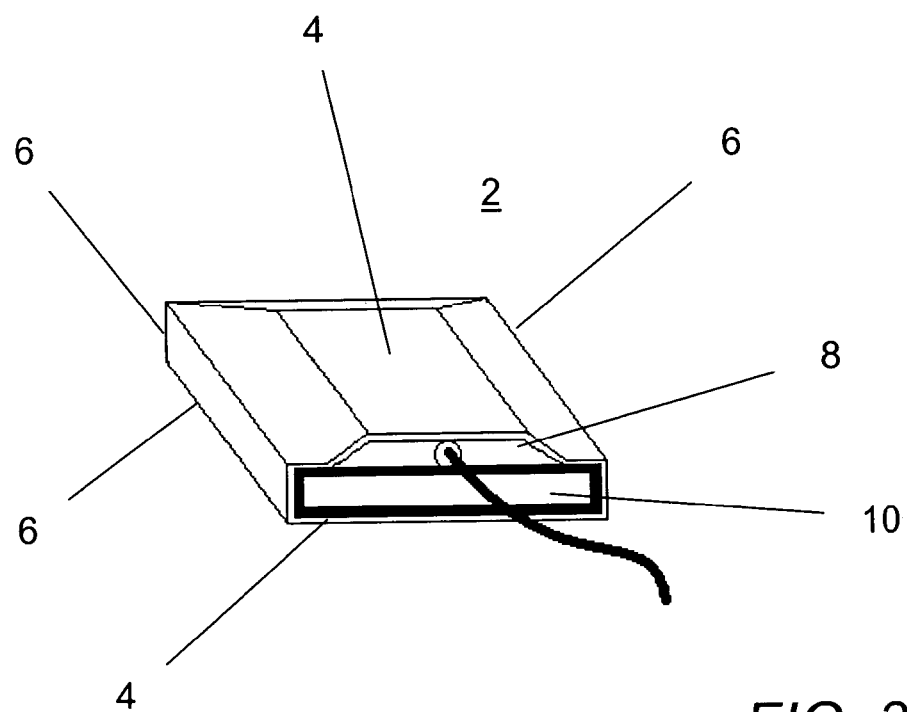
FIG. 3 is a perspective view of the digital dental x-ray sensor protector having a digital dental x-ray sensor inserted therein in accordance with an embodiment of the present invention.

FIG. 2 and FIG. 3 show a digital dental x-ray sensor protector 2 for use in combination with a digital dental x-ray sensor 10 for reducing damage to such a sensor and pain to a patient associated with the placement of such a sensor into the oral cavity of the patient. Dental x-ray protector 2, formed in a single molding operation, comprises two flexible, substantially rectangular wall members 4 secured to one another by a perimeter wall member 6 and having a perimeter slot 8. The perimeter wall member 6 may have one, two, three or more components so as to substantially connect the wall members 4 to form a sleeve.

Perimeter slot 8 is typically of a dimension which is about the same size as a digital dental x-ray sensor to be inserted. By forming perimeter slot 8 with a diameter about the same as a digital dental x-ray sensor, one can provide a digital dental x-ray sensor protector which will snugly fit around the digital dental x-ray sensor to thereby hold the sensor firmly within the protector without the need to use adhesive materials or cushioning.

Use of dental x-ray sensor protector 2 is as follows. A digital sensor 10 is placed inside dental x-ray sensor protector 2 through perimeter slot 8. Dental x-ray sensor protector 2 and associated sensor 10 are then placed into the oral cavity of a patient. Digital dental x-ray sensor protector 2 acts as an anti-septic barrier between sensor 10 and the patient's oral cavity. The sensor is then exposed to gamma radiation, and the sensor transmits signals used to form an image on a computer for image processing. Digital dental x-ray sensor protector 2 and associated sensor 10 are then removed from the oral cavity of a patient, and the sensor 10 is removed from dental x-ray sensor protector 2. Dental x-ray sensor protector 2 can then be sterilized and reused or, alternatively, simply discarded.

Although digitized dental x-ray sensor protector 2 is shown in roughly the shape of a digital dental x-ray sensor known in the art, there is no requirement that the device of the present invention be shaped as such. The digital dental x-ray sensor protector can take many shapes and still function in accordance with the present invention, for example, the protector may be formed as a square, octagon, hexagon or any suitable shape which will allow a dental x-ray sensor to snugly fit entirely within the protector for protection and yet provide sufficient comfort to a patient when the protector and associated sensor are placed in the oral cavity of the patient.

Digital dental x-ray sensor protector 2 is preferably made from medical grade plastic. However, it should be appreciated by those skilled in the art that the device may be formed from any of a number of resilient, non-toxic materials, such as polyurethane foam, silicone foam, polyethylene foam, highly plasticized polyvinylchloride, silicone gel, and the like. Other foams or non-foams having suitable elastic and/or plastic properties to ensure protection, comfort and minimal toxicity may also be used.

The materials, of course, must be sterilizable in order to be employed within an oral cavity. However, many plastic materials are sterilizable, either by autoclaving or by radiation sterilization. For repeated reuse of a dental x-ray sensor protector in the context of a dental or veterinary office, it may be desirable to formulate the protector of medical grade plastic. This may be desirable in that most dental or veterinary offices have an autoclave readily available for sterilization, medical grade plastic being sterilization by autoclaving.

Digital dental x-ray sensor protector 2 may be fabricated in various sizes to correspond to the various sizes of digital dental x-ray sensors available. Moreover, digital dental x-ray sensor protector 2 can be flavored or colored to any desirable taste or color to improve its aesthetic character and to improve its acceptance by a patient. Coloring may be employed as means of color coding the various sizes to readily indicate the size of sensor adapted to fit within a particular sensor protector.

Digital dental x-ray sensor protector 2 may be fabricated by any technique known in the art for the fabrication of small tubular members formed of foam or non-foam materials of the type mentioned. For example, injection molding or blow-molding are believed to work well in this regard Digital dental x-ray sensor protector 2 may also be attached to a holder for digital dental x-ray sensor 10. Various types of holders are known in the art. Digital dental x-ray sensor protector 2 may then be used as a positioning aid by a dentist or dental technician or veterinarian, ensuring that sensor 10 will be properly positioned in a patient's oral cavity.

In describing exemplary embodiments, specific terminology is employed for the sake of clarity in this disclosure. However, the disclosure of this patent specification is not intended to be limited to the specific terminology so selected and it is to be understood that each specific element includes all technical equivalents that operate in a similar manner.

In addition, the above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A removable digital dental x-ray sensor protector comprising:
   two flexible, substantially rectangular wall members, said wall members secured to one another by a perimeter wall member, said wall members made from materials having suitable properties to ensure comfort when the protector is used intra-orally; and
   a perimeter slot, said slot adapted to receive a digital dental x-ray sensor, and to contain said sensor entirely between said wall members, said wall members protecting said sensor from moisture, biting, and other potentially damaging factors that occur when the sensor is used intra-orally;
   wherein said rectangular and perimeter wall members exert a resilient force on said sensor inserted into said protector through said slot to hold said sensor firmly within the protector without the need to use adhesive materials;
   wherein said protector alleviates the need to sterilize the sensor after each use; and
   wherein said protector serves to reduce or avoid the pain or discomfort caused by sharp edges and corners of the sensor.

2. The digital dental x-ray sensor protector of claim 1 wherein said protector is made of medical grade plastic.

3. The digital dental x-ray sensor protector of claim 1 wherein said protector is formed in a single piece to form a sleeve.

4. The digital dental x-ray sensor protector of claim 1 wherein said protector is auto-clavable or heat-sterilized.

5. The digital dental x-ray sensor protector of claim 1 wherein said protector is an anti-septic barrier.

6. The digital dental x-ray sensor protector of claim 1 wherein said protector is attached to a holder, such that said protector is used as a positioning aid by the user.

7. A method of using a removable digital dental x-ray sensor protector comprising the steps of:
   providing a protector comprised of two flexible, substantially rectangular wall members, said flexible wall members secured to one another by a perimeter wall member and having a perimeter slot, said slot adapted to receive a dental x-ray sensor;
   inserting the sensor through the perimeter slot of said protector, such that said sensor is contained entirely between said wall members and wherein said rectangular and perimeter wall members exert a resilient force on said sensor inserted into said protector through said slot to hold said sensor firmly within the protector without the need to use adhesive materials;

protecting the sensor from moisture, biting, and other potentially damaging factors when used intra-orally, alleviating the need to sterilize the sensor after each use, and reducing pain or discomfort caused by sharp edges and corners of the sensor;

placing the digital dental x-ray sensor protector and said contained sensor into an oral cavity of a patient;

imaging the patient's tooth;

removing said protector and contained sensor from the oral cavity; and removing said sensor from said protector for further processing.

* * * * *